(12) United States Patent
Park

(10) Patent No.: US 11,918,706 B2
(45) Date of Patent: Mar. 5, 2024

(54) COMPOSITION FOR BONE DEFECT AND PREPARATION METHOD OF THE SAME AND KIT FOR THE SAME

(71) Applicant: MedPark Co.,Ltd, Busan (KR)

(72) Inventor: JungBok Park, Busan (KR)

(73) Assignee: MedPark Co.,Ltd, Busan (KR)

( * ) Notice: Subject to any disclaimer, the term of this patent is extended or adjusted under 35 U.S.C. 154(b) by 0 days.

(21) Appl. No.: 16/908,661

(22) Filed: Jun. 22, 2020

(65) Prior Publication Data
US 2021/0046222 A1 Feb. 18, 2021

(30) Foreign Application Priority Data

Aug. 14, 2019 (KR) .................. 10-2019-0099244
Sep. 24, 2019 (KR) .................. 10-2019-0117675

(51) Int. Cl.
| | | |
|---|---|---|
| *A61L 27/56* | (2006.01) | |
| *A61L 2/08* | (2006.01) | |
| *A61L 2/20* | (2006.01) | |
| *A61L 27/20* | (2006.01) | |
| *A61L 27/36* | (2006.01) | |

(52) U.S. Cl.
CPC .............. *A61L 27/56* (2013.01); *A61L 2/081* (2013.01); *A61L 2/206* (2013.01); *A61L 27/20* (2013.01); *A61L 27/3608* (2013.01); *A61L 27/3687* (2013.01); *A61L 2202/21* (2013.01); *A61L 2430/02* (2013.01)

(58) Field of Classification Search
CPC ........ A61L 27/56; A61L 2/0281; A61L 2/206; A61L 27/20; A61L 27/3608; A61L 2202/21; A61L 2430/02
See application file for complete search history.

(56) References Cited

U.S. PATENT DOCUMENTS

2011/0117166 A1   5/2011   Melican

FOREIGN PATENT DOCUMENTS

| CN | 1220168 A | 6/1999 |
|---|---|---|
| KR | 10-2002-0014034 A | 2/2002 |
| KR | 10-0401941 B1 | 10/2003 |
| KR | 10-2012-0097521 A | 9/2012 |
| KR | 10-2015-0006507 A | 1/2015 |
| KR | 10-2017-0015802 A | 2/2017 |
| KR | 10-1779377 B1 | 9/2017 |
| KR | 10-2019-0016522 A | 2/2019 |
| KR | 10-1959523 B1 | 3/2019 |

OTHER PUBLICATIONS

Microscope Master, Laboratory Centrifuge Guide, 2017; screen shot from WayBack Machine of https://web.archive.org/web/20170603024815/https://www.microscopemaster.com/laboratory-centrifuge.html (Year: 2017).*

(Continued)

*Primary Examiner* — Bethany P Barham
*Assistant Examiner* — Ayaan A Alam
(74) *Attorney, Agent, or Firm* — Insight Law Group, PLLC; Seung Lee

(57) ABSTRACT

The present disclosure relates to a bone graft composition, and more particularly, to a bone graft composition containing a porous bone graft material and hydroxypropyl methylcellulose.

9 Claims, 1 Drawing Sheet

(56) References Cited

OTHER PUBLICATIONS

Centrix, Snap-Fit Syringe, 2017; screenshot from WayBack Machine of https://web.archive.org/web/20170225225904/htttps://www.centrixdental.com/snap-fit-syringe.html (Year: 2017).*
Oh, S. H., Creating growth factor gradients in three dimensional porous matrix by centrifugation and surface immobilization, 2011, Elsevier, biomaterials, 32, 8254-8260 (Year: 2011).*
Decision to grant a patent dated Apr. 17, 2020 from Korean Industrial Property Office for Korean Patent Application No. 10-2019-0117675 and its English translation.
Notice of Preliminary Rejection dated Dec. 19, 2019 from Korean Industrial Property Office for Korean Patent Application No. 10-2019-0117675 and its English translation.

* cited by examiner

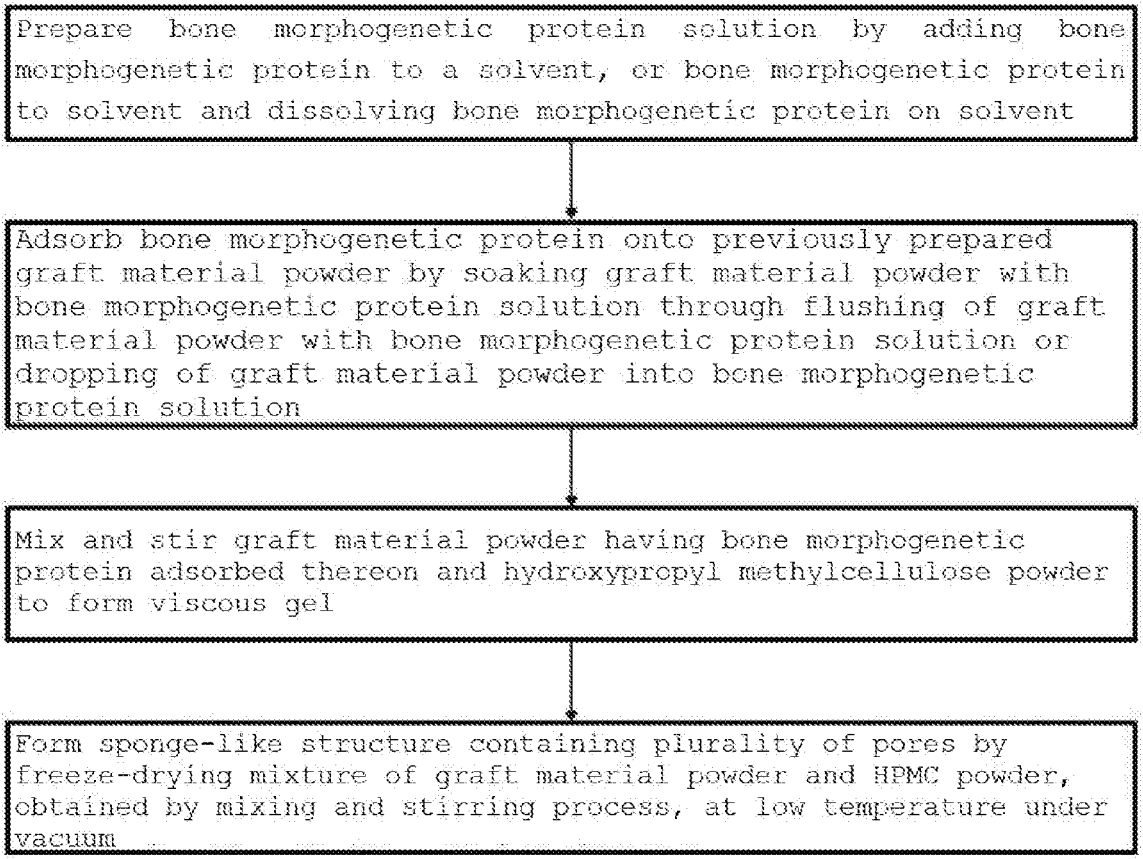

COMPOSITION FOR BONE DEFECT AND PREPARATION METHOD OF THE SAME AND KIT FOR THE SAME

CROSS-REFERENCE TO RELATED APPLICATION(S)

This application claims priority to Korean Patent Application No. 10-2019-0099244, filed on Aug. 14, 2019, and Korean Patent Application No. 10-2019-0117675, filed on Sep. 24, 2019, the disclosures of which are incorporated herein by reference in their entirety.

BACKGROUND OF THE DISCLOSURE

Technical Field

The present disclosure relates to a bone graft composition, a preparation method therefor, and a bone graft composition kit.

Description of the Related Art

Various materials and various methods may be used for reconstruction of defective bone. For example, bone graft materials such as bone powders, bone chips, and bone blocks may be used, or methods such as autografting, allografting, and xenografting may be used for reconstruction of defective bone.

Bone graft materials that are used for reconstruction of defective bone may be used in orthopedic surgery, neurosurgery, plastic surgery, otolaryngology, Oral and Maxillofacial Surgery, Department of Veterinary Medicine (veterinary clinic), dermatology and dentistry. For example, these materials may be used for bone defects during disc surgery to induce bone regeneration, or may also be used for implant surgery and reconstruction of oral and maxillofacial bone defects.

Meanwhile, Korean Patent No. 10-0401941 discloses technology related to a bone graft material and a preparation method therefor. When a reticular bone is used which is composed of bioceramic powder and has a three-dimensionally communicating pore structure as disclosed therein, there may be limitations in the effect of bone graft in terms of biocompatibility, mechanical properties, toxicity, and the like.

Prior Art Documents

Patent Documents (Patent Document 0001) Korean Patent No. 10-0401941

SUMMARY

An object of the present disclosure is to provide a bone graft composition, a preparation method therefor, and a bone graft composition kit, which have excellent effects in terms of activation of bone formation, biocompatibility, and ease of use.

The present disclosure provides the followings:

1. A bone graft composition containing a porous bone graft material and hydroxypropyl methylcellulose.
2. The bone graft composition of 1, wherein the porous bone graft material is a natural bone graft material.
3. The bone graft composition of 1, wherein the content of the hydroxypropyl methylcellulose is 0.15 to 6 parts by weight based on 1 part by weight of the porous bone graft material.
4. The bone graft composition of 1, wherein the composition includes a sponge-like structure containing a porous structure.
5. A bone graft composition kit including: the bone graft composition of any one of 1 to 4, and a syringe containing the bone graft composition.
6. A method for preparing a bone graft composition, the method including steps of:

preparing a bone morphogenetic protein solution by adding a bone morphogenetic protein to a solvent, or the bone morphogenetic protein to the solvent and dissolving the bone morphogenetic protein on the solvent;

adsorbing the bone morphogenetic protein onto previously prepared graft material powder by soaking the graft material powder with the bone morphogenetic protein solution through flushing of the graft material powder with the bone morphogenetic protein solution or dropping of the graft material powder into the bone morphogenetic protein solution;

mixing and stirring the graft material powder having the bone morphogenetic protein adsorbed thereon and hydroxypropyl methylcellulose powder to form a viscous gel; and forming a sponge-like structure containing a plurality of pores by freeze-drying the mixture of the graft material powder and the hydroxypropyl methylcellulose powder, obtained by the mixing and stirring process, at a low temperature under vacuum.

7. The method of 6, wherein the bone morphogenetic protein is at least one selected from the group consisting of BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, recombinant bone morphogenetic proteins thereof, and bone morphogenetic proteins equivalent thereto.
8. The method of 6, wherein the concentration of the bone morphogenetic protein in the bone morphogenetic protein solution is 0.05 to 0.15 mg/ml.
9. The method of 8, wherein the pH of the bone morphogenetic protein solution is adjusted using phosphate buffer saline.
10. The method of 6, wherein the step of adsorbing the bone morphogenetic protein onto the graft material powder includes a step of adsorbing the bone morphogenetic protein using a refrigerated centrifuge.
11. The method of 10, wherein the rotational speed of the refrigerated centrifuge is 4,000 rpm or more.
12. The method of 10, wherein the step of adsorbing the bone morphogenetic protein using the refrigerated centrifuge is performed at a cold temperature of 5° C. or below.
13. The method of 6, wherein the volume ratio between the graft material powder having the bone morphogenetic protein adsorbed thereon and the hydroxypropyl methylcellulose powder is 1:0.2 to 1:0.6.
14. The method of 6, further including a step of placing the prepared bone graft composition including a sponge-like structure containing a plurality of pores in a snap tube sized to be inserted into a syringe.
15. The method of 14, further including a step of placing and sealing the bone graft composition including a sponge-like structure containing a plurality of pores, placed in the snap tube, in a syringe.

16. The method of 6, further including a step of sterilizing the bone graft composition including a sponge-like structure containing a plurality of pores by ethylene oxide gas or gamma-ray irradiation.

17. The method of 16, wherein the concentration of the ethylene oxide gas is 450 to 1,200 mg/l, or the dose of the gamma-ray irradiation is 10 to 25 kGy.

BRIEF DESCRIPTION OF THE DRAWINGS

FIG. 1 is a flow diagram schematically showing a method for preparing a bone graft composition according to one embodiment of the present disclosure.

DESCRIPTION OF SPECIFIC EMBODIMENTS

Embodiments of the present disclosure relate to a bone graft composition which may have excellent effects in terms of activation of bone formation, biocompatibility, and ease of use by containing a porous bone graft material and hydroxypropyl methylcellulose.

However, description of a portion of a particular embodiment, which overlaps with that of other embodiments, will be omitted for a clearer and more concise explanation. Even though description of that portion is omitted, the portion is not excluded from the present disclosure and the scope of rights thereof should be admitted in the same manner as that of other embodiments.

In the following description, the detailed description of publicly-known technology related to the present disclosure will be omitted when it may unnecessarily obscure the subject matter of the present disclosure. In addition, the terms used in the following description are terms defined in consideration of their functions in the present disclosure and may be changed according to the intention of a user or an operator, or according to practice. Therefore, the definitions of these terms should be determined based on the contents throughout the specification.

The technical spirit of the present disclosure is determined by the claims, and the following embodiments are merely means for efficiently explaining the technical spirit of the present disclosure to those skilled in the art to which the present disclosure pertains.

In the present disclosure, when the repeating unit, compound or resin represented by a formula includes isomers thereof, the corresponding formula representing the repeating unit, compound or resin means a representative formula that also represents the isomers.

Hereinafter, specific embodiments of the present disclosure will be described. However, these embodiments are only examples, and the present disclosure is not limited thereto.

The bone graft composition may be implanted into a bone defect, and may be used to restore the bone defect by filling the bone defect. Hereinafter, 'implant' includes being applied into a bone defect in the state of not having rigidity or in the state of having rigidity. Applying into a bone defect in the state of having rigidity may being implanted into a bone defect after being formed the shape corresponding to the shape of the bone defect in the state of having rigidity by a shape forming device, for example 3 dimensional printer.

A bone graft composition of the present disclosure contains a porous bone graft material and hydroxypropyl methylcellulose. The bone graft composition may be implanted into a bone defect, and may be used to restore the bone defect by filling the bone defect.

The bone graft material may be natural bone, for example, autogenous bone, allogeneic bone, or xenogenic bone. When the natural bone is used, it may exhibit an excellent bone formation effect, because it has excellent biocompatibility and also has good wettability and hygroscopicity due to a large number of pores contained therein. In addition, the natural bone may also be used for reconstruction of defective bone in orthopedic surgery, neurosurgery, plastic surgery, otolaryngology, Oral and Maxillofacial Surgery, Department of Veterinary Medicine (veterinary clinic), dermatology and dentistry.

In addition, the bone graft material may also be used for reconstruction of defective bone in human or animals. Hereinafter, it mainly described the usage to the dentistry, however, the usage does not limited thereto.

As the bone graft composition contains hydroxypropyl methylcellulose, the bone graft composition may have adhesion to a bone defect. When the bone graft composition has excellent adhesion, even if the bone graft composition is applied to the maxilla, it may not flow down, and even if there is an impact due to mastication motion, the bone graft composition may be prevented from being detached from the bone defect.

According to one embodiment of the present disclosure, the content of the hydroxypropyl methylcellulose in the bone graft composition may be 0.15 to 6 parts by weight, preferably 0.2 to 0.4 parts by weight, based on 1 part by weight of the porous bone graft material. If the content of the hydroxypropyl methylcellulose is less than 0.15 parts by weight based on 1 part by weight of the porous bone graft material, the bone graft composition may have insufficient adhesion to a bone defect, and thus may be highly likely to be detached from the bone defect during use. On the other hand, if the content of the hydroxypropyl methylcellulose is more than 6 parts by weight based on 1 part by weight of the porous bone graft material, the hydroxypropyl methylcellulose may interfere with bone formation by interfering with the wettability, hygroscopicity or the like of xenogenic bone.

A bone graft composition kit according to another embodiment of the present disclosure includes the above-described bone graft composition and a syringe containing the composition. By providing the syringe directly containing the bone graft composition, it is possible to ensure ease of use and significantly reduce the possibility of contamination that may occur during use.

However, in the description of this embodiment, the description of a portion that overlaps with that of other embodiments is omitted for a clearer and more concise explanation. Even though the description of that portion is omitted, the portion is not excluded from the present disclosure and the scope of rights thereof should be admitted in the same manner as that of other embodiments.

A method for preparing a bone graft composition according to still another embodiment of the present disclosure includes steps of:
  preparing a bone morphogenetic protein solution by adding a bone morphogenetic protein to a solvent, or the bone morphogenetic protein to the solvent and dissolving the bone morphogenetic protein on the solvent;
  adsorbing the bone morphogenetic protein onto previously prepared graft material powder by soaking the graft material powder with the bone morphogenetic protein solution through flushing of the graft material powder with the bone morphogenetic protein solution or dropping of the graft material powder into the bone morphogenetic protein solution;

mixing and stirring the graft material powder having the bone morphogenetic protein adsorbed thereon and hydroxypropyl methylcellulose powder to form a viscous gel; and forming a sponge-like structure containing a plurality of pores by freeze-drying the mixture of the graft material powder and the hydroxypropyl methylcellulose powder, obtained by the mixing and stirring process, at a low temperature under vacuum. The bone graft composition prepared through these steps may have excellent effects in terms of activation of bone formation, biocompatibility, and ease of use.

However, in the description of this embodiment, the description of a portion that overlaps with that of the above-described embodiments is omitted for a clearer and more concise explanation. Even though the description of that portion is omitted, the portion is not excluded from the present disclosure and the scope of rights thereof should be admitted in the same manner as that of the above-described embodiments.

FIG. 1 is a flow diagram schematically showing a method for preparing a bone graft composition according to one embodiment of the present disclosure.

First, a bone morphogenetic protein solution is prepared by dissolving a bone morphogenetic protein in a solvent. The bone morphogenetic protein solution may be prepared by adding the bone morphogenetic protein to the solvent, or adding the bone morphogenetic protein to the solvent and dissolving the bone morphogenetic protein in the solvent.

The bone morphogenetic protein may be at least one selected from the group consisting of BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, recombinant bone morphogenetic proteins thereof, and bone morphogenetic proteins equivalent thereto. Preferably, the bone morphogenetic protein may be rhBMP-2 in terms of the bone formation effect of the present disclosure.

According to one embodiment of the present disclosure, the concentration of the bone morphogenetic protein in the bone morphogenetic protein solution may be 0.05 to 0.15 mg/ml, preferably 0.08 to 0.12 mg/ml. When the concentration of the bone morphogenetic protein is within the above-described range, bone formation by the bone morphogenetic protein may be activated. If the concentration of the bone morphogenetic protein is less than 0.05 mg/ml, the ability of the bone morphogenetic protein to form new bone may be reduced, and if the concentration of the bone morphogenetic protein is more than 0.15 mg/ml, it may cause adverse effects.

In addition, according to one embodiment of the present disclosure, the pH of the bone morphogenetic protein solution may be, for example, 4.6 to 5. When the pH is within the above-described range, bone formation by the bone morphogenetic protein may be activated. If the pH of the bone morphogenetic protein solution is less than 4.6, the ability of the bone morphogenetic protein to form new bone may be reduced, and if the pH of the bone morphogenetic protein solution is more than 5, the ability of the bone morphogenetic protein to form new bone may be reduced. For example, the pH may be adjusted using phosphate buffer saline. When the pH is adjusted using phosphate buffer saline, the bone morphogenetic protein may have the effect of forming new bone.

Thereafter, the bone morphogenetic protein is adsorbed onto graft material powder by soaking the graft material powder with the bone morphogenetic protein solution. The previously prepared graft material powder may be soaked with the bone morphogenetic protein solution by flushing the graft material powder with the bone morphogenetic protein solution or dropping the graft material powder into the bone morphogenetic protein solution, whereby the bone morphogenetic protein may be adsorbed onto the graft material powder.

The graft material powder may be autogenous bone, allogeneic bone, or xenogenic bone. For example, the graft material powder may be prepared by placing it in a snap tube.

The average particle diameter (D50) of the graft material powder may be 200 to 5,000 μm, preferably 250 to 1,000 μm. If the average particle diameter of the powder is less than 200 μm, the graft material may be absorbed rapidly, and thus osteoconduction required for bone formation may be insufficient, and if the average particle diameter of the powder is more than 5,000 μm, precise processing of the graft material powder during application to a patient may be difficult.

According to one embodiment of the present disclosure, the step of adsorbing the bone morphogenetic protein onto the graft material powder may include a step of adsorbing the bone morphogenetic protein using a refrigerated centrifuge.

In some cases, the bone morphogenetic protein may also be suspended in the solution. However, when the bone morphogenetic protein is adsorbed while it is rotated at high speed using a centrifuge, the bone morphogenetic protein can be prevented from being suspended in the solution, and thus the bone morphogenetic protein may be easily adsorbed onto the surface or into the pores of the graft material powder. Only when the bone morphogenetic protein is adsorbed while it is rotated at high speed, it can be prevented from being suspended again after detachment from the graft material powder. If the bone morphogenetic protein is rotated at low speed, it can be suspended, and hence cannot be easily adsorbed. Under high-speed rotation, the bone morphogenetic protein can be adsorbed quickly onto the surface or into the pores of the graft material powder.

According to one embodiment of the present disclosure, the rotational speed of the refrigerated centrifuge may be 4,000 rpm or more. When the bone morphogenetic protein is adsorbed using the centrifuge, the higher the rotational speed, the better the adsorption. For example, the rotational speed of the centrifuge may be 4,000 rpm or more, and when this rotational speed range is satisfied, the bone morphogenetic protein can be prevented from being suspended in the solution.

According to one embodiment of the present disclosure, the step of adsorbing the bone morphogenetic protein using the refrigerated centrifuge may be performed at a cold temperature of 5° C. or below. As the step of adsorbing the bone morphogenetic protein using the refrigerated centrifuge is performed at a cold temperature of 5° C. or below, it is possible to maximize the effect of adsorbing the bone morphogenetic protein onto the surface or into the pores of the graft material powder through rotation while preventing the denaturation of the bone morphogenetic protein that is weak to heat, by preventing the temperature of the solution from being increased due to rotation. The cold temperature may be a temperature at which the solution does not freeze. For example, the cold temperature may be 5° C. or below, preferably 0.5 to 1.5° C.

Thereafter, the graft material powder having the bone morphogenetic protein adsorbed thereon and hydroxypropyl methylcellulose powder are mixed and stirred to form a gel. The viscous gel thus formed can improve the adhesion of the graft material powder. For example, the stirring may be performed using a mixer. As the graft material powder is stirred with the hydroxypropyl methylcellulose in powder form, a product with homogeneous quality can be obtained.

According to one embodiment of the present disclosure, the volume ratio between the graft material powder having the bone morphogenetic protein adsorbed thereon and the hydroxypropyl methylcellulose powder may be 1:0.2 to 1:0.6. If the volume ratio of the hydroxypropyl methylcellulose powder is less than 0.2, it may be difficult to form a gel, and if the volume ratio of the hydroxypropyl methylcellulose powder is more than 0.6, it may be difficult to form an effective bone graft composition because the volume of the gel is larger than the volume of the graft material powder. In terms of the effects of the present disclosure, the volume ratio between the graft material powder having the bone morphogenetic protein adsorbed thereon and the hydroxypropyl methylcellulose powder may preferably be 1:0.25 to 1:0.35.

Thereafter, the mixture of the graft material powder and the hydroxypropyl methylcellulose powder, obtained by the mixing and stirring process, is freeze-dried under vacuum to form a sponge-like structure containing pores. A sponge-like structure containing a plurality of pores may also be formed by freeze-drying the mixture of the graft material powder and the hydroxypropyl methylcellulose powder, obtained by the mixing and stirring process, at a low temperature under vacuum.

A sponge-like structure including a porous structure may be formed by the freeze-drying treatment under vacuum. The gel may be absorbed into the graft material powder to form a sponge-like structure including a porous structure, and it is believed that the treatment under vacuum mainly contributes to the formation of the sponge-like structure including a porous structure.

According to one embodiment of the present disclosure, the method for preparing the bone graft composition may further include a packaging step.

According to one embodiment of the present disclosure, the method for preparing the bone graft composition may further include a step of placing the prepared bone graft composition including a sponge-like structure containing a plurality of pores in a snap tube sized to be inserted into a syringe. When the method further includes the step of placing the composition in a snap tube sized to be inserted into a syringe, the composition may be sized to be inserted into the syringe and thus may be inserted directly into the syringe without a separate process, so that the operation of the process for preparing the bone graft composition can be facilitated.

According to an embodiment of the present disclosure, the method for preparing the bone graft composition may further include a step of placing and sealing the bone graft composition including a sponge-like structure containing a plurality of pores, placed in the snap tube, in a syringe. When the bone graft composition is provided in the syringe, it is possible to ensure ease of use and significantly reduce the possibility of contamination that may occur during use.

According to one embodiment of the present disclosure, the method for preparing the bone graft composition may further include a step of sterilizing the composition.

In one embodiment of the present disclosure, the bone graft composition including a sponge-like structure containing a plurality of pores may be sterilized by ethylene oxide gas. For example, the concentration of the ethylene oxide gas may be 450 to 1,200 mg/l. If the concentration of the ethylene oxide gas is less than 450 mg/l, sterilization may be insufficient, and if the concentration of the ethylene oxide gas is more than 1,200 mg/l, denaturation of the bone morphogenetic protein may occur.

According to one embodiment of the present disclosure, the bone graft composition including a sponge-like structure containing a plurality of pores may be sterilized by gamma-ray irradiation. For example, the dose of the gamma-ray irradiation may be 10 to 25 kGy. If the dose of the gamma-ray irradiation is less than 10 kGy, sterilization may be insufficient, and if the dose of the gamma-ray irradiation is more than 25 kGy, denaturation of the bone morphogenetic protein may occur.

Hereinafter, preferred examples will be presented to help the understanding of the present disclosure. However, these examples are merely to illustrate the present disclosure and are not intended to limit the scope of the present disclosure as defined in the appended claims. In addition, it will be obvious to those skilled in the art that various changes and modifications of these examples are possible without departing from the scope and technical spirit of the present disclosure. In addition, it is to be understood that these changes and modifications also fall within the appended claims.

Experimental Examples

1. Wettability of Graft Materials 0.1 ml, 0.2 ml and 0.3 ml of blood were dropped onto the edges of each of allogeneic bone, xenogeneic bone and synthetic bone as graft materials, and whether the graft materials absorbed the blood well was observed. The results are shown in Table 1 below.

TABLE 1

| Samples | Graft materials | Graft material volume (cc) | Graft material weight (g) | Blood amount (pig)/ml | | |
|---|---|---|---|---|---|---|
| | | | | 0.1 | 0.2 | 0.3 |
| 1 | Allogeneic bone | 0.3 | 0.3 | ○○ | ○○ | ○○ |
| 2 | Xenogeneic bone | 0.3 | 0.15 | ○ | ○ | ○ |
| 3 | Synthetic bone | 0.3 | 0.3 | Δ | Δ | Δ |

○○: excellent, ○: good, Δ: moderate
Each experiment was performed 10 times for each blood amount.

All the graft materials had good blood absorption abilities, but the synthetic bone could not trap the blood therein, and thus the bone formation ability thereof was reduced. It could be confirmed that blood played an important role in bone formation, and the wettability of the graft materials improved the bone formation effect.

2. Wettability Depending on Ratio Between Bone Graft Material and Hydroxypropyl Methylcellulose Bone graft compositions were prepared by adding hydroxypropyl methylcellulose to each of allogeneic bone, xenogeneic bone and synthetic bone at various ratios (each experiment was performed 100 times for each ratio). The content of each of the bone graft materials and hydroxypropyl methylcellulose and the results depending thereon are shown in Tables 2 to 4 below.

TABLE 2

| Examples | Graft material (allogeneic bone) volume (cc) | Hydroxy-propyl methyl-cellulose volume (cc) | Graft material (allogeneic bone) weight (g) | Hydroxy-propyl methyl-cellulose weight (g) | Suitability |
|---|---|---|---|---|---|
| A-1 | 0.3 | 0.03 | 0.3 | 0.02 | Unsuitable |
| A-2 | 0.3 | 0.08 | 0.3 | 0.05 | Suitable |
| A-3 | 0.3 | 0.13 | 0.3 | 0.09 | Suitable |
| A-4 | 0.3 | 0.2 | 0.3 | 0.13 | Suitable |
| A-5 | 0.3 | 0.3 | 0.3 | 0.19 | Suitable |
| A-6 | 0.3 | 0.45 | 0.3 | 0.29 | Suitable |
| A-7 | 0.3 | 0.7 | 0.3 | 0.46 | Suitable |
| A-8 | 0.3 | 1.2 | 0.3 | 0.78 | Suitable |
| A-9 | 0.3 | 2.7 | 0.3 | 1.77 | Suitable |

TABLE 3

| Examples | Graft material (xenogeneic bone) volume (cc) | Hydroxy-propyl methyl-cellulose volume (cc) | Graft material (xenogeneic bone) weight (g) | Hydroxy-propyl methyl-cellulose weight (g) | Suitability |
|---|---|---|---|---|---|
| B-1 | 0.3 | 0.03 | 0.15 | 0.02 | Unsuitable |
| B-2 | 0.3 | 0.08 | 0.15 | 0.05 | Suitable |
| B-3 | 0.3 | 0.13 | 0.15 | 0.09 | Suitable |
| B-4 | 0.3 | 0.2 | 0.15 | 0.13 | Suitable |
| B-5 | 0.3 | 0.3 | 0.15 | 0.19 | Suitable |
| B-6 | 0.3 | 0.45 | 0.15 | 0.29 | Suitable |
| B-7 | 0.3 | 0.7 | 0.15 | 0.46 | Suitable |
| B-8 | 0.3 | 1.2 | 0.15 | 0.78 | Suitable |
| B-9 | 0.3 | 2.7 | 0.15 | 1.77 | Suitable |

TABLE 4

| Examples | Graft material (synthetic bone) volume (cc) | Hydroxy-propyl methyl-cellulose volume (cc) | Graft material (synthetic bone) weight (g) | Hydroxy-propyl methyl-cellulose weight (g) | Suitability |
|---|---|---|---|---|---|
| C-1 | 0.3 | 0.03 | 0.3 | 0.02 | Unsuitable |
| C-2 | 0.3 | 0.08 | 0.3 | 0.05 | Suitable |
| C-3 | 0.3 | 0.13 | 0.3 | 0.09 | Suitable |
| C-4 | 0.3 | 0.2 | 0.3 | 0.13 | Suitable |
| C-5 | 0.3 | 0.3 | 0.3 | 0.19 | Suitable |
| C-6 | 0.3 | 0.45 | 0.3 | 0.29 | Suitable |
| C-7 | 0.3 | 0.7 | 0.3 | 0.46 | Suitable |
| C-8 | 0.3 | 1.2 | 0.3 | 0.78 | Suitable |
| C-9 | 0.3 | 2.7 | 0.3 | 1.77 | Suitable |

It was confirmed that the hydroxypropyl methylcellulose was suitably formed into a putty when the weight thereof was 0.05 g or more, and the weight of the hydroxypropyl methylcellulose that maximizes the wettability of the graft materials ranged from 0.05 to 0.13 g. The blood-wettability of the graft materials may be an important factor in relation to the formation of new bone in a bone defect.

3. Adhesion of Graft Materials

Dental maxillary models were prepared, and the molar tooth portion was set as a missing portion. Each of putty-type bone graft materials was implanted (adhered) into the missing portion, and then blood (20 cc/hr) was allowed to influence the missing portion through a feeding back supply container. Experiments were performed on each of allogeneic bone, xenogeneic bone and synthetic bone (each experiment was performed 100 times for each ratio), and the content of each component and the results depending thereon are shown in Tables 5 to 7 below.

TABLE 5

| Examples | Graft material (allogeneic bone) volume (cc) | Hydroxy-propyl methyl-cellulose volume (cc) | Graft material (allogeneic bone) weight (g) | Hydroxy-propyl methyl-cellulose weight (g) | Suitability |
|---|---|---|---|---|---|
| A-0 | 0.3 | 0 | 0.3 | 0 | Unsuitable |
| A-1 | 0.3 | 0.03 | 0.3 | 0.02 | Unsuitable |
| A-2 | 0.3 | 0.08 | 0.3 | 0.05 | 5 min or more |
| A-3 | 0.3 | 0.13 | 0.3 | 0.09 | 5 min or more |
| A-4 | 0.3 | 0.2 | 0.3 | 0.13 | 5 min or more |
| A-5 | 0.3 | 0.3 | 0.3 | 0.19 | 5 min or more |
| A-6 | 0.3 | 0.45 | 0.3 | 0.29 | 5 min or more |
| A-7 | 0.3 | 0.7 | 0.3 | 0.46 | 5 min or more |
| A-8 | 0.3 | 1.2 | 0.3 | 0.78 | 5 min or more |
| A-9 | 0.3 | 2.7 | 0.3 | 1.77 | 5 min or more |

TABLE 6

| Examples | Graft material (xenogeneic bone) volume (cc) | Hydroxy-propyl methyl-cellulose volume (cc) | Graft material (xenogeneic bone) weight (g) | Hydroxy-propyl methyl-cellulose weight (g) | Suitability |
|---|---|---|---|---|---|
| B-0 | 0.3 | 0 | 0.15 | 0 | Unsuitable |
| B-1 | 0.3 | 0.03 | 0.15 | 0.02 | Unsuitable |
| B-2 | 0.3 | 0.08 | 0.15 | 0.05 | 5 min or more |
| B-3 | 0.3 | 0.13 | 0.15 | 0.09 | 5 min or more |
| B-4 | 0.3 | 0.2 | 0.15 | 0.13 | 5 min or more |
| B-5 | 0.3 | 0.3 | 0.15 | 0.19 | 5 min or more |
| B-6 | 0.3 | 0.45 | 0.15 | 0.29 | 5 min or more |
| B-7 | 0.3 | 0.7 | 0.15 | 0.46 | 5 min or more |
| B-8 | 0.3 | 1.2 | 0.15 | 0.78 | 5 min or more |
| B-9 | 0.3 | 2.7 | 0.15 | 1.77 | 5 min or more |

TABLE 7

| Examples | Graft material (synthetic bone) volume (cc) | Hydroxy-propyl methyl-cellulose volume (cc) | Graft material (synthetic bone) weight (g) | Hydroxy-propyl methyl-cellulose weight (g) | Suitability |
|---|---|---|---|---|---|
| C-0 | 0.3 | 0 | 0.3 | 0 | Unsuitable |
| C-1 | 0.3 | 0.03 | 0.3 | 0.02 | Unsuitable |
| C-2 | 0.3 | 0.08 | 0.3 | 0.05 | 5 min or more |
| C-3 | 0.3 | 0.13 | 0.3 | 0.09 | 5 min or more |
| C-4 | 0.3 | 0.2 | 0.3 | 0.13 | 5 min or more |
| C-5 | 0.3 | 0.3 | 0.3 | 0.19 | 5 min or more |
| C-6 | 0.3 | 0.45 | 0.3 | 0.29 | 5 min or more |
| C-7 | 0.3 | 0.7 | 0.3 | 0.46 | 5 min or more |
| C-8 | 0.3 | 1.2 | 0.3 | 0.78 | 5 min or more |
| C-9 | 0.3 | 2.7 | 0.3 | 1.77 | 5 min or more |

Considering that the time required for the suture performed by a medical operator after implantation of a graft material in actual clinical practices is 2 to 5 minutes, the adhesion of each bone graft material for each Example was tested. From all the experimental results for the putty-type bone graft materials, it could be confirmed that all the samples containing 0.05 g or more of the HPMC maintained adhesion for 5 minutes or more.

In addition, it could be confirmed that when the content of the putty-type graft material was 0.2 to 0.4 parts by weight based on 1 part by weight of the porous bone graft material, it exhibited desirable effects.

As described above, the bone graft composition, the preparation method therefor or the bone graft composition kit according to the present disclosure may have excellent effect in terms of activation of bone formation, biocompatibility, and ease of use.

What is claimed is:

1. A method for preparing a bone graft composition, the method comprising steps of:
    preparing a bone morphogenetic protein solution by adding a bone morphogenetic protein to a solvent, or the bone morphogenetic protein to the solvent and dissolving the bone morphogenetic protein on the solvent;
    adsorbing the bone morphogenetic protein onto previously prepared graft material powder by soaking the graft material powder with the bone morphogenetic protein solution through flushing of the graft material powder with the bone morphogenetic protein solution or dropping of the graft material powder into the bone morphogenetic protein solution;
    mixing and stirring the graft material powder having the bone morphogenetic protein adsorbed thereon and hydroxypropyl methylcellulose powder to form a viscous gel;
    wherein adsorbing the bone morphogenetic protein onto the graft material powder comprises a step of adsorbing the bone morphogenetic protein using a refrigerated centrifuge; and
    forming a sponge-like structure containing a plurality of pores by freeze-drying the mixture of the graft material powder and the hydroxypropyl methylcellulose powder, obtained by the mixing and stirring process, at a low temperature under vacuum,
    wherein the step of adsorbing the bone morphogenetic protein using the refrigerated centrifuge is performed at a cold temperature of 5° C. or below; and
    wherein the volume ratio between the graft material powder having the bone morphogenetic protein adsorbed thereon and the hydroxypropyl methylcellulose powder is 1:0.25 to 1:0.35.

2. The method of claim 1, wherein the bone morphogenetic protein is at least one selected from the group consisting of BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, recombinant bone morphogenetic proteins thereof.

3. The method of claim 1, wherein the concentration of the bone morphogenetic protein in the bone morphogenetic protein solution is 0.05 to 0.15 mg/ml.

4. The method of claim 3, wherein a pH of the bone morphogenetic protein solution is adjusted using phosphate buffer saline.

5. The method of claim 1, wherein the rotational speed of the refrigerated centrifuge is 4,000 rpm or more.

6. The method of claim 1, further comprising a step of placing the prepared bone graft composition including a sponge-like structure containing a plurality of pores in a snap tube sized to be inserted into a syringe.

7. The method of claim 6, further comprising a step of placing and sealing the bone graft composition including a sponge-like structure containing a plurality of pores, placed in the snap tube, in a syringe.

8. The method of claim 1, further comprising a step of sterilizing the bone graft composition including a sponge-like structure containing a plurality of pores by ethylene oxide gas or gamma-ray irradiation.

9. The method of claim 8, wherein the concentration of the ethylene oxide gas is 450 to 1,200 mg/l, or the dose of the gamma-ray irradiation is 10 to 25 kGy.

* * * * *